US00PP26917P3

(12) United States Plant Patent
Wright et al.

(10) Patent No.: US PP26,917 P3
(45) Date of Patent: Jul. 12, 2016

(54) BLUEBERRY PLANT NAMED 'C03-158'

(50) Latin Name: ***Vaccinium corymbosum* hybrid**
Varietal Denomination: C03-158

(71) Applicants: CostaExchange Pty Ltd., Corindi (AU); Florida Foundation Seed Producers, Inc., Marianna, FL (US)

(72) Inventors: Gary Wright, Corindi Beach (AU); Paul Lyrene, Miscanopy, FL (US)

(73) Assignees: Costaexchange PTY Ltd, Corindi (AU); Florida Foundation Seed Producers, Inc., Marianna, FL (US)

( * ) Notice: Subject to any disclaimer, the term of this patent is extended or adjusted under 35 U.S.C. 154(b) by 14 days.

(21) Appl. No.: 13/999,286

(22) Filed: Feb. 6, 2014

(65) Prior Publication Data

US 2014/0223618 P1 Aug. 7, 2014

Related U.S. Application Data

(60) Provisional application No. 61/849,974, filed on Feb. 6, 2013.

(51) Int. Cl.
*A01H 5/08* (2006.01)

(52) U.S. Cl.
USPC ..... Plt./157
CPC ..... *A01H 5/08* (2013.01)

(58) Field of Classification Search
USPC ..... Plt./157
See application file for complete search history.

(56) References Cited

U.S. PATENT DOCUMENTS

PP12,165 P2 10/2001 Lyrene

OTHER PUBLICATIONS

PLUTO Plant Variety Database Jun. 20, 2015.*
Plant Variety Journal 2011 vol. 24 No. 4 Australia.*

* cited by examiner

*Primary Examiner* — Annette Para
(74) *Attorney, Agent, or Firm* — Hahn Loeser & Parks, LLP

(57) ABSTRACT

A new and distinct cultivar of blueberry (*Vaccinium corymbosum* hybrid) plant named 'C03-158', characterized by its strong plant growth vigor, low chilling requirement, medium timing of fruiting, medium fruit size, firm fruit suited to handling, good fruit flavor. This combination results in higher quality fruit with a later availability than other varieties.

3 Drawing Sheets

Latin name of the family, genus, and species:
Family—Ericaceae.
Genus—*Vaccinium.*
Species—*corymbosum* hybrid.
Variety denomination: The new blueberry plant claimed is of the variety denominated 'C03-158'.

BACKGROUND OF THE INVENTION

The present invention relates to a new and distinct perennial variety of *Vaccinium corymbosum* hybrid (blueberry), which has been given the variety denomination of 'C03-158'. The new variety 'C03-158' shows distinctive traits such as early season, good flavor and firm fruit. Its market class is that of a fruiting plant. The new variety 'C03-158' is intended for use as fresh fruit for shipping, customer pick and processing markets and as a home garden plant.

The new blueberry cultivar is a selection resulting from seedlings produced in a controlled breeding programme of *Vaccinium* varieties in Florida, USA in 2001 from a cross of the blueberry variety known as 'Emerald' (seed parent) (U.S. Plant Pat. No. 12,165) and the blueberry variety known as 'F97-169' (pollen parent) (unpatented). The seed from the cross was sown and grown in Corindi Beach, New South Wales, Australia. The new cultivar was discovered and selected in 2003 as a single plant within a population of seedlings resulted from the controlled cross, in an experimental block in the field at Corindi Beach, New South Wales, Australia, and has since been named 'C03-158'. Selection criteria were a combination of early season, low chilling requirement, medium fruit of good flavor, firm fruit. The new variety was subsequently evaluated for a number of years at the commercial farm at Corindi Beach, New South Wales, Australia. The new variety showed distinctive traits such as mid-season, good flavor and firm fruit.

Asexual reproduction of the new variety 'C03-158' by softwood cutting propagation since 2003 at Corindi Beach, New South Wales, Australia has demonstrated that the new variety reproduces true to type with all of the characteristics, as herein described, firmly fixed and retained through successive generations of such asexual propagation, with the clones phenotypically identical to the original plant.

The seed parent 'Emerald' is characterized by a late-very late timing of ripening of fruit. The pollen parent 'F97-169' is characterized by an early timing of ripening of fruit. The new variety 'C03-158' differs from the seed parent 'Emerald' in that 'C03-158' has an earlier cropping timing, averaging 30 days earlier than 'Emerald'. The new variety 'C03-158' has maintained its distinguished characteristics throughout successive asexual propagation.

SUMMARY OF THE INVENTION

The new variety 'C03-158' was originated from a cross of 'Emerald' (seed parent) and the variety known as 'F97-169' (pollen parent) in 2001 in Florida, USA. The seed parent is characterized by a mid to late timing of ripening of fruit. The pollen parent is characterized by an early timing of ripening of fruit.

The new blueberry variety resulted from seedlings produced in a controlled breeding programme. The cross was made in 2001 in Florida, USA and the seed was sown and grown on in Corindi Beach, NSW, Australia.

The new variety was selected in 2003 from among plants located on land at Corindi Beach and has since been named 'C03-158'. Since then plants of 'C03-158' were propagated by cuttings for further evaluation and resulted to be uniform and stable. Asexual reproduction of the new variety 'C03-158' by cutting propagation since 2003 at Corindi Beach, NSW, Australia has demonstrated that the new variety reproduces true to type plants.

The new variety was selected in 2003 as a single plant within a population of seedlings resulting from controlled cross of *Vaccinium* varieties. The seedling population was planted in an experimental block in the field at Corindi Beach, NSW, Australia and the selection of the new variety took place in the same block. Selection criteria were a combination of early season, low chilling requirement, medium fruit of good flavour, firm fruit. The new variety was subsequently evaluated for a number of years at the commercial farm at Corindi Beach, NSW, Australia.

The following characteristics of the new variety have been repeatedly observed and can be used to distinguish 'C03-158' as a new and distinct variety of *Vaccinium corymbosum* hybrid:

1. medium fruiting season
2. strong plant vigor
3. medium fruit size
4. good flavor
5. firm fruit Plants of the new variety 'C03-158' differ from plants of the seed parent 'Emerald' primarily in that 'C03-158' has a medium season cropping timing, averaging 30 days earlier than 'Emerald'. The new blueberry variety 'C03-158' has maintained its distinguished characteristics throughout successive asexual propagation. The variety has been repeatedly asexually reproduced thought softwood cuttings in NSW, Australia and the clones are phenotypically identical to the original plant.

BRIEF DESCRIPTION OF THE DRAWINGS

The accompanying photographic illustration shows typical specimens in full color of the foliage and fruit of the new variety 'C03-158'. The colors are as nearly true as is reasonably possible in a color representation of this type.

Figure 1:
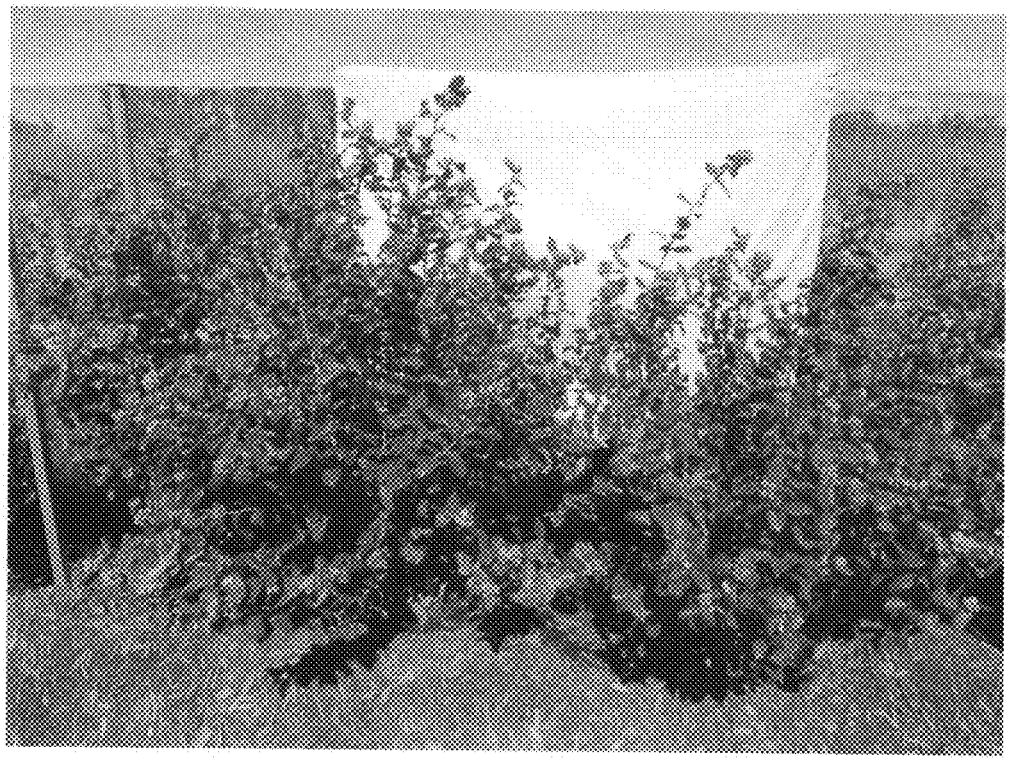
FIG. 1 is a photograph of the new variety 'C03-158', demonstrating the plant's strong vigor.
Figure 2:
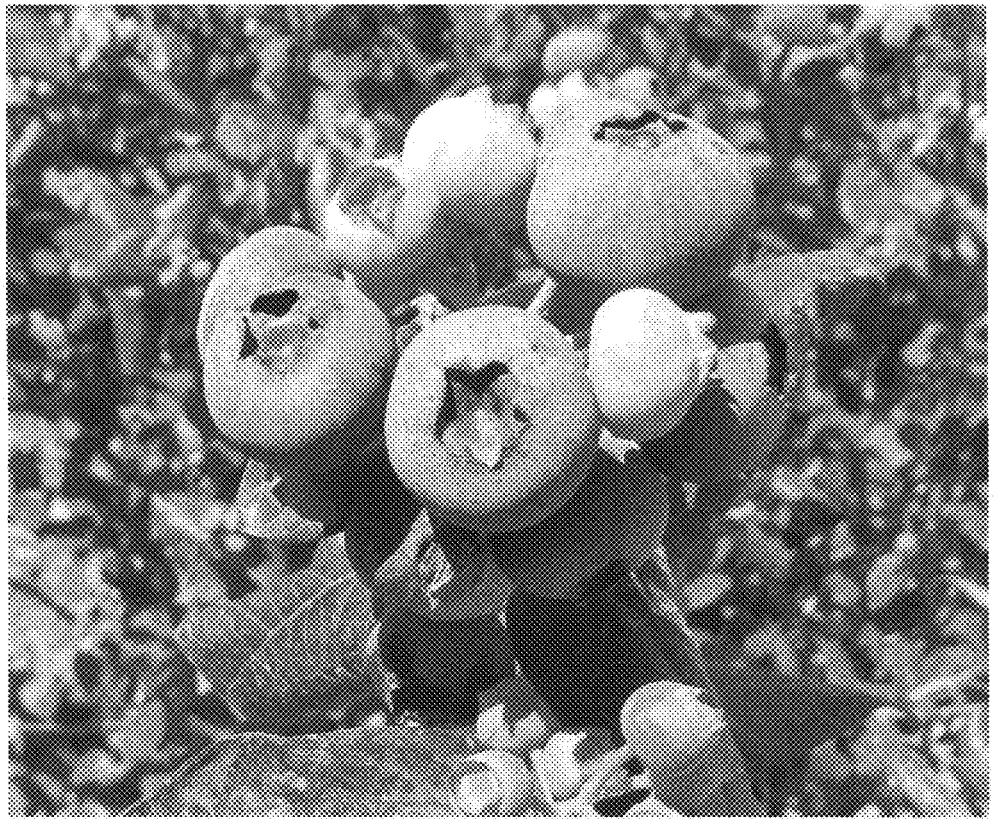
FIG. 2 is a photograph of the fruit of the new variety 'C03-158'.
Figure 3:
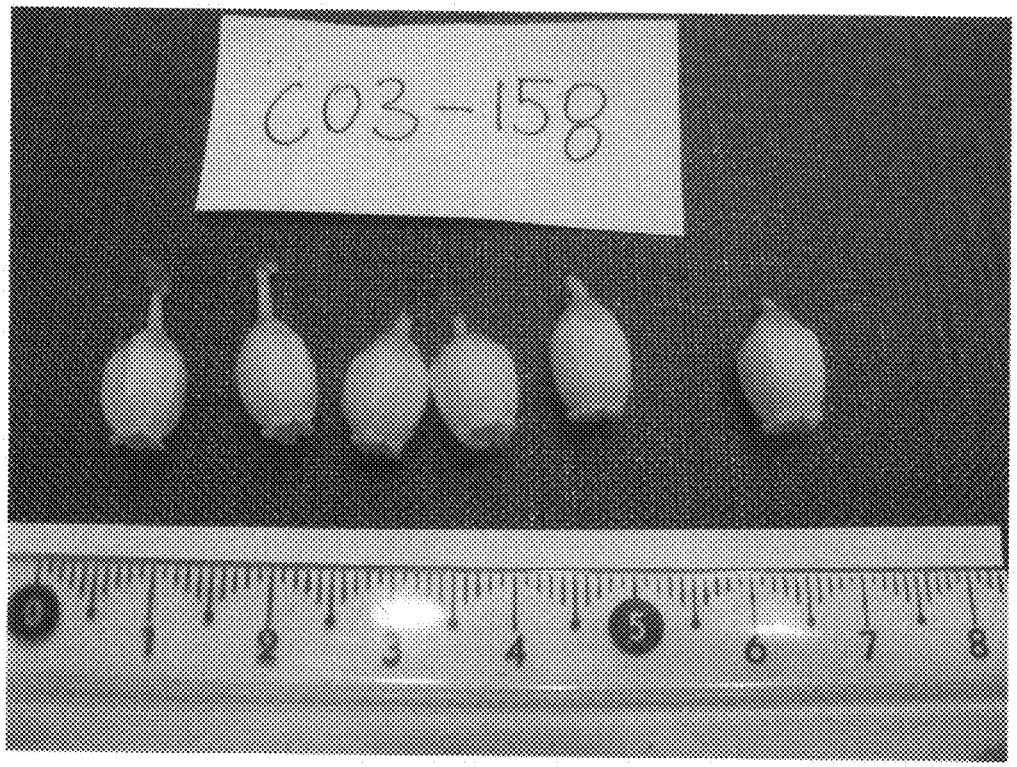
FIG. 3 is a photograph of the flowers of the new variety 'C03-158'.

The colors in the photographs are as close as possible with the photographic and printing technology utilized. The color values cited in the detailed botanical description accurately describe the colors of the new blueberry.

DETAILED BOTANICAL DESCRIPTION

The following detailed description sets forth the distinctive characteristics of 'C03-158'. The data which defines these characteristics was collected from asexual reproductions of the original selection. Dimensions, sizes, colors, and other characteristics are approximations and averages set forth as accurately as possible. The plant history was taken on plants approximately 5 years of age, and the descriptions relate to plants grown in the field in Corindi Beach, New South Wales Australia. Descriptions of fruit characteristics were made on fruit grown in Corindi Beach, New South Wales Australia. Color designations are from R.H.S. Chart—edition 2007.

Classification:

*Family*.—Ericaceae.
*Genus*.—*Vaccinium*.
*Species*.—*Corymbosum* hybrid.
*Common name*.—Blueberry.

Parentage:

*Seed parent*.—'Emerald' (U.S. Plant Pat. No. 12,165).
*Pollen parent*.—'F97-169' (unpatented).

Market class: Suitable for the Commercial, Hand Harvest Fresh, Processed, and Home Garden Markets.

PLANT

General:

*Parentage*.—'Emerald'×'F97-169'.
*Plant height*.—1.90 m.
*Plant width*.—1.21 m.
*Growth habit*.—Upright.
*Growth*.—Vigorous.
*Productivity*.—High.
*Cold hardiness*.—Low.
*Cold tolerance*.—Low to medium.
*Chilling requirement*.—Low.
*Tolerance to disease*.—Mild susceptibility to leaf rust.
*Leafing*.—Abundant.
*Twigginess*.—Medium.

STEM

General:

*Suckering tendency*.—Low.
*Mature cane color*.—Greyed brown group 199C.
*Mature cane length*.—1.1 m.
*Mature cane width*.—12 mm.
*Bark texture*.—Medium (between smooth and rough).
*Surface texture of new wood*.—Smooth.
*Internode length on strong, new shoots*.—23.6 mm.
*Fruiting wood*.—18.8 cm in length.

FOLIAGE

General:

*Time of beginning of leaf bud burst*.—Early to medium.
*Leaf color* (*top side*).—Green group 139 A.
*Leaf color* (*under side*).—Green group N138B.
*Leaf arrangement*.—Alternate.
*Leaf shape*.—Elliptic.
*Leaf margins*.—Entire.
*Undulation of margin*.—Weak.
*Leaf venation*.—Reticulate.
*Leaf apices*.—Acute.
*Leaf bases*.—Rounded.
*Leaf length*.—75 mm.
*Leaf width*.—39.9 mm.
*Leaf length/width ratio*.—1.9.
*Leaf nectarines*.—Absent.
*Pubescence of upper side*.—Absent.
*Pubescence of lower side*.—Absent.

*Cross sectional profile*.—Flat.
*Longitudinal profile*.—Straight.
*Attitude*.—Horizontal.

Petioles:
*Length*.—4.1 mm.
*Width*.—1.8 mm.
*Color*.—Green group 143C.

FLOWERS

General:
*Time of beginning of flowering*.—Medium.
*Time of* 50% *anthesis*.—3rd August.
*Flower shape*.—Urceolate.
*Flower bud density*.—Medium.
*Flower fragrance*.—Little.
*Flower arrangement*.—Alternately.
*Flower type*.—Complete flower, having sepals, petals, stamens and pistils.

Corolla:
*Color*.—White group 155A.
*Length*.—7.2 mm.
*Width*.—7.6 mm.
*Aperture width*.—5.5 mm.
*Anthocyanin coloration of corolla*.—Absent.
*Corolla ridges*.—Present.
*Protrusion of stigma*.—Absent.
*Shape*.—Urceolate.

Inflorescence:
*Length*.—Ranging between 12 to 19 mm.
*Diameter*.—Ranging between 15 to 22 mm.
*Length of peduncle*.—14 mm.
*Surface texture of peduncle*.—Smooth.
*Color of peduncle*.—Yellow green group 144C.
*Length of pedicel*.—4.2 mm.
*Surface texture of pedicel*.—Smooth.
*Color of pedicel*.—Yellow green group 144C.
*Number of flowers per cluster*.—7.
*Flower cluster density*.—Medium to dense.

Calyx (with sepals):
*Diameter*.—7.2 mm.

Stamen:
*Length*.—8 mm.
*Number per flower*.—10.
*Filament color*.—Yellow-green group 145C.
*Style*.—Length — 9.2 mm.
*Color*.—Yellow-green group 145C.

Pistil:
*Length*.—12 mm.
*Ovary color* (*exterior*).—Green group 143C.

Anther:
*Length*.—4.3 mm.
*Number*.—10.
*Color*.—Greyed-orange group 165B.

Pollen:
*Abundance*.—Medium.
*Color*.—Yellow group 4D.
*Self-compatibility*.—Possible, but with the result of smaller fruit sizes, averaging 1 g compared to cross pollinated (2.5 g).

FRUIT

General:
*Time of fruit ripening*.—Medium.
*Time of* 50% *maturity*.—5th October.
*Fruit development period*.—63 days.
*Cluster density*.—Medium.
*Unripe fruit color*.—Yellow-green group 144B.
*Ripe berry color*.—Blue group 102B.
*Berry surface wax abundance*.—Strong.
*Berry flesh color*.—Yellow-green group 145B.
*Berry weight*.—2.5 g.
*Berry height from calyx to scar*.—11.84 mm.
*Berry diameter*.—16.36 mm.
*Berry shape*.—Oblate.
*Fruit stem scar*.—Medium to small.
*Sweetness when ripe*.—Medium
*Firmness when ripe*.—Firm.
*Acidity when ripe*.—Medium to low.
*Storage quality*.—Medium to long.
*Suitability for mechanical harvesting*.—Not tested.
*Self-fruitfulness*.—Medium.
*Uses*.—Fresh fruit.
*Number of berries per cluster*.—6.

SEED

General:
*Seed abundance in fruit*.—High, 250 seeds in 10 fruit.
*Seed color*.—Greyed-orange group N167A.
*Seed length*.—2.35 mm.

COMPARISON BETWEEN PARENTAL AND COMMERCIAL CULTIVARS

| | | Comparator variety | | | | |
|---|---|---|---|---|---|---|
| Characteristic | Variety C03-158 | C99-042 | Emerald | C97-390 | Star | Snowchaser |
| Soluble solid content (%) | 11.4 | 13.1 | 11.6 | 12.2 | 13.1 | 14.3 |
| Titratable acidity (%) | 0.4 | 0.3 | 0.5 | 0.3 | 0.4 | 0.5 |
| Fruit weight (g) | 2.5 | 1.9 | 3.0 | 2.0 | 1.9 | 1.7 |
| Plant habit | Upright | Semi-upright to spreading | Spreading | Semi-upright | Strongly upright to upright | Semi-upright |
| Time of fruit ripening | Mid-season | Early | Mid to late | Early | Late | Very early |

The invention claimed is:

1. A new and distinct variety of blueberry plant named 'C03-158', substantially as illustrated and described herein.

* * * * *